United States Patent [19]

Meisberger et al.

[11] Patent Number: 4,925,299
[45] Date of Patent: May 15, 1990

[54] HEMOGLOBIN DETECTOR

[75] Inventors: Artur Meisberger; Hans-Jürgen Neumann, both of St. Wendel, Fed. Rep. of Germany

[73] Assignee: Fresenius AG, Bad Homburg, Fed. Rep. of Germany

[21] Appl. No.: 229,599

[22] Filed: Aug. 8, 1988

[30] Foreign Application Priority Data

Aug. 10, 1987 [DE] Fed. Rep. of Germany ....... 3726524

[51] Int. Cl.$^5$ ............................................. G01N 33/48
[52] U.S. Cl. ........................................ 356/40; 128/633
[58] Field of Search .................... 356/40, 41; 128/633, 128/665, 664

[56] References Cited

U.S. PATENT DOCUMENTS 4,447,150  5/1984  Heinemann .......................... 356/41
4,773,422  9/1988  Isaacson et al. ..................... 128/633

*Primary Examiner*—Léon Scott, Jr.
*Attorney, Agent, or Firm*—Townsend and Townsend

[57] ABSTRACT

A photoelectric arrangement for the determination of a substance spectrally differently absorbing light in a specimen (1) comprising two alternately switched on light sources (2,3) of different wavelengths matched to the absorption maximum or minimum of the substance, two photoelectric receivers (5,6) arranged in such a manner with respect to the specimen that the one receiver (measuring receiver 5) receives light which traverses the specimen and the other receiver (reference receiver 6) receives light of the light sources directly and an electronic control and evaluation circuit following the photoelectric receivers and controlling the light sources for the determination of the different absorption typical for the substance at the two wavelengths, wherein the control and evaluation circuit comprises a light circuit (7,8,10,11a,11b) following the reference receiver (6) for determining light amounts transmitted by the light sources and defining the switchover instant for the light sources on reaching a predetermined amount of light.

10 Claims, 2 Drawing Sheets

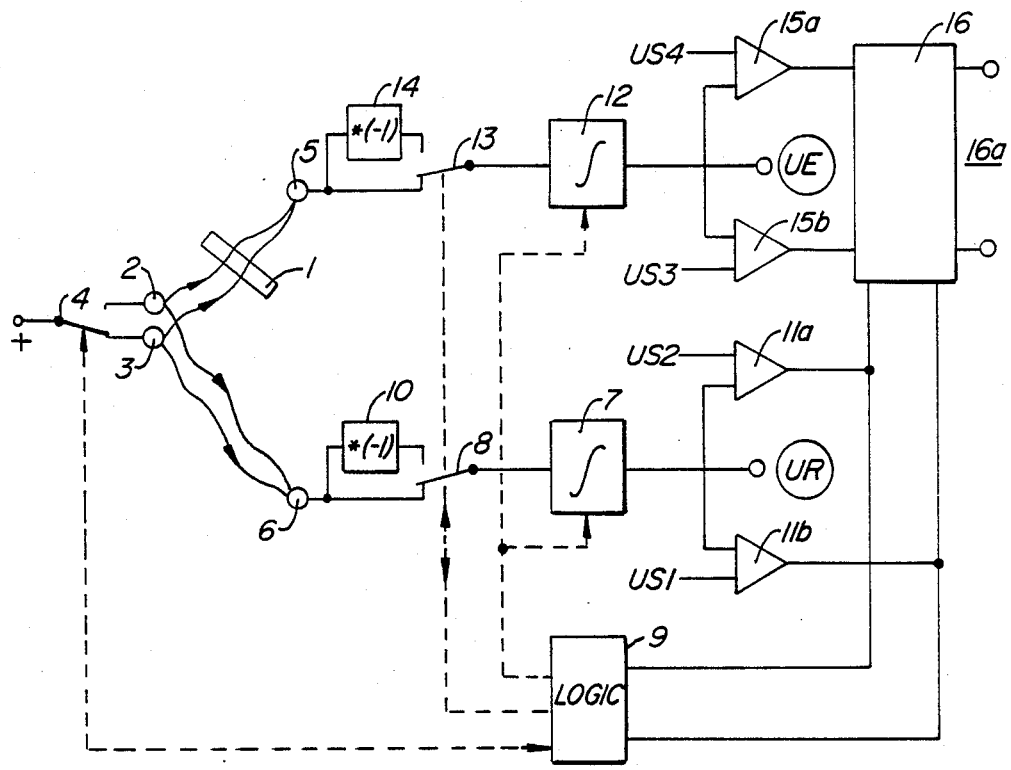
FIG._1.
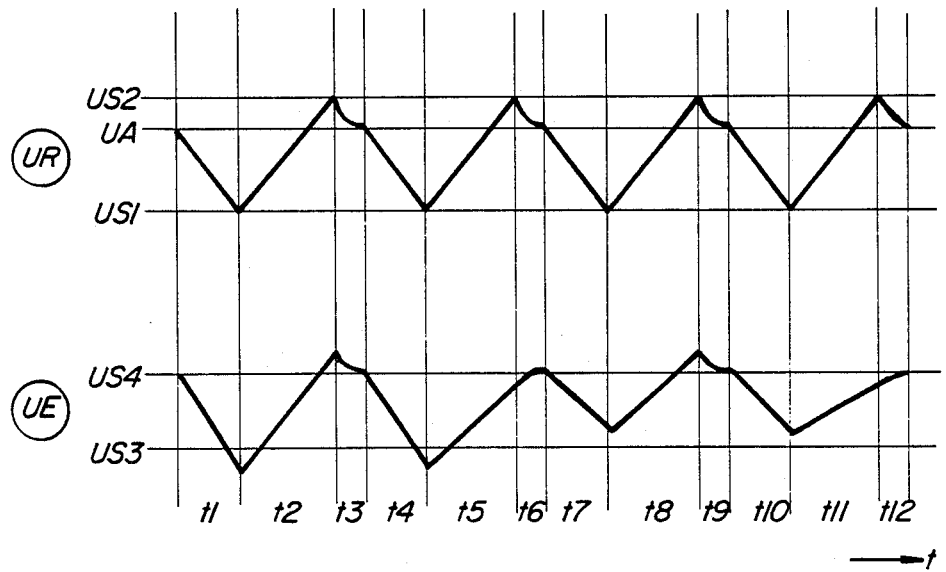
FIG._2.

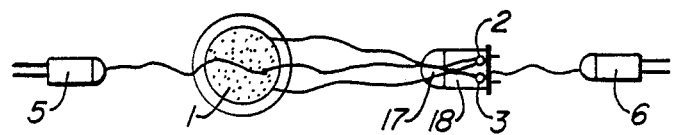
FIG._3a.
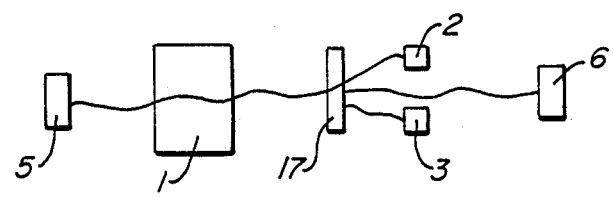
FIG._3b.
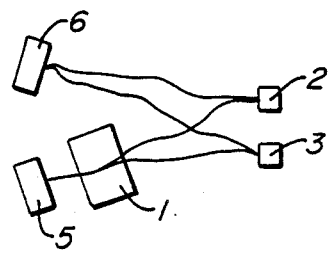
FIG._3c.

HEMOGLOBIN DETECTOR

DESCRIPTION

The invention relates to a photoelectric arrangement for the determination of a substance spectrally differently absorbing light in a specimen comprising two alternately switched on light sources of different wavelengths matched to the absorption maximum or minimum of the substance, two photoelectric receivers arranged in such a manner with respect to the specimen that the one receiver (measuring receiver) receives light which traverses the specimen and the other receiver (reference receiver) receives light of the light sources directly and an electronic control and evaluation circuit following the photoelectric receivers and controlling the light sources for the determination of the different absorption typical for the substance at the two wavelengths.

Such an arrangement is known from the PCT publication with the international publication no. WO 81/02633.

Arrangements of the type mentioned above serve for example for the determination of hemoglobin or of red blood corpuscles in plasma or another fluid, also in comparatively low concentration. The two wavelengths then lie typically in the red or in the green spectral area.

In the known case a beam splitter is provided which conducts a part of the light of the two light sources directly onto the one photoelectric receiver (reference receiver) and another part onto the specimen from where the light passes to the second receiver (measuring receiver).

The determination of the substance is by the determination of the absorption ratio on transmission of the light through the specimen in the individual spectral areas. For this purpose an electronic control and evaluation circuit which operates by sampling, i.e. is clocked is provided and which works in the following manner: The two light sources are alternately switched on with comparatively high frequency (1 KHz), i.e. a momentary measurement is made in the individual spectral areas. The intensity of the one (first) light source is set at a predetermined value (reference value) with a first sampling circuit; the output signal of the reference receiver on receiving the light of the first light source serves here as an actual value signal. With a second sampling circuit the intensity of the other (second) light source is set in such a manner that the amounts of light detected by the measuring receiver alternately in the two spectral areas are equal. This intensity value of the second light source, measured at the reference receiver in the associated cycle and in relation to the predetermined reference value of the intensity of the first light source, is a measure of the absorption ratio sought which is evaluated by a further circuit.

This known arrangement comprises considerable disadvantages.

The known measuring principle is based on a comparison of instantaneous intensity values and is thus very intensity-critical. The intensity of the light sources is however greatly temperature-dependent, in particular with the modern components, light-emitting diodes (LED), which are preferably used in the above arrangement; even small temperature variations influence considerably the beam yield of the LEDs. Although the intensity of the one light source is held at a constant value, an exact measurement is not possible with the known arrangement.

In addition, the beam splitter used is exposed to contaminations differently affecting the intensity of the light fluxes, which likewise falsify the measurement.

In addition, the principle of double wavelength spectrophotometry is known as such from Angewandte Chemie, vol. 88 (1976), pages 750–755. The disclosure does not however discuss the problem underlying the invention, let alone provide hints for its solution.

German specification as laid open to inspection No. 2,363,432 shows a specific diffused light turbidimeter having two light sources and two receivers separated by diaphragms in such a manner that each receiver is impinged upon by the transmitted light as well as by the diffused light of the respective other light source. The concentration of the liquids in the specimen can be determined from the four measured radiation intensities. This optical apparatus also obviously has no direct similarities to that according to the aforementioned PCT disclosure.

Finally the German specification as laid open to inspection No. 3,218,102 describes an optical apparatus for the measurement of radiation absorption by single-wave spectrophotometry with which a control measurement can be carried out with the aid of a second receiver without specimen. A reference to a light quantity control of two light sources and the switching over of the two light sources associated therewith cannot be derived from this publication.

The problem underlying the invention is to further develop the arrangement referred to at the beginning in such a manner that the accuracy of the measurement is considerably increased.

The solution to this problem is achieved proceeding from the arrangements referred to at the beginning according to the invention in that the control and evaluation circuit comprises a light circuit following the reference receiver for determining the light amounts transmitted by the light sources and defining the switch-over instant for the light sources on reaching a predetermined amount of light.

Through the step according to the invention of standardizing the light quantities irradiated by the light sources fluctuations in the intensity of the light sources or secondary light sources (beam splitter) have no interfering influence on the measurement result. The accuracy of the measurement is thus considerably increased.

With the aid of the examples of embodiment illustrated in the drawings the invention and its developing features will be described in detail.

In the drawings:

FIG. 1 shows an example of embodiment of a photoelectric arrangement for the determination of a substance spectrally differently absorbing light in a specimen, FIG. 2 shows the voltage curves at two typical points of the circuit arrangement according to FIG. 1 and FIG. 3 shows the different arrangement possibilities of the photoelectric elements with respect to the specimen.

The FIG. 1 shows a photoelectric arrangement for the determination of a substance spectrally differently absorbing light and contained in a specimen 1. The arrangement comprises two light sources 2,3 having different wavelengths and being alternately activatable by means of a changeover switch 4. The wavelengths are expediently matched to the absorption maximum or minimum of the substance. Should for example the substance to be examined be hemoglobin, then the one wavelength will be 565 nm (green light) and the other wavelength 635 nm (red light). In addition, two photoelectric receivers 5,6 are provided, aligned in such a manner with respect to the specimen 1 that the receiver 6—called reference receiver—directly receives the light of both sources, whereas the receiver 5—called measuring receiver—receives the light which has passed through the specimen. The light quantities reaching the receivers are converted into proportional voltage values. The measuring receiver detects the light quantities influenced by the specimen by absorption. The associated voltage values in the individual spectral areas contain information on the clouding of the specimen and on the presence of substances which influence the different light colour to different degrees.

Furthermore, the arrangement comprises a control and evaluation circuit following the photoelectric receivers and controlling the light sources for the determination of the absorptions typically different for the substance at the two wavelengths, which will be described in the following. The control and evaluation circuit comprises firstly a light circuit following the reference receiver 6 for determining the light quantities transmitted by the light sources and defining the instant of switchover for the light sources on reaching a predetermined light quantity. An integrator 7 is provided which is connectable via a changeover switch 8 which is controlled synchronously via a light source changeover switch 4 by a control logic 9, either directly or indirectly via a sign reversing member 10 to the output of the reference receiver 6. A threshold value arrangement consisting of two operational amplifiers 11a,11b acting as comparators and having different threshold values US1 and US2 follows the integrator 7. The threshold values predefine certain light quantities, the exceeding of which is detected by the control logic. The output signal UR of the integrator 7 with respect to the said threshold values is illustrated in FIG. 2, row 1.

The actual measuring circuit of the control and evaluation arrangement is formed by an arrangement of the same type; a further integrator 12 is provided which is connectable via a changeover switch 13, which is controlled synchronously with the other changeover switches 4,8 by the control logic 9, either directly or indirectly via a sign reversing member 14 to the output of the measuring receiver 5. A threshold value arrangement consisting of two comparators 15a,15b with different threshold values US3 and US4 follows the integrator 12. An evaluation logic 16 follows the threshold value arrangement and detects the magnitude of the integrator output signal UE with respect to the said threshold values—as illustrated in FIG. 2, row 2, for different conditions in order to detect the different absorption in the spectral areas as indicator for the presence of a particular substance, which is shown by a corresponding signal at the output 16a of the evaluation logic.

The arrangement described above operates in the following manner:

At the beginning the circuit is assumed to be in the illustrated state, i.e. the light source 3 is switched on and the changeover switches 8,13 are connected at the lower contact directly to the respective receiver. Proceeding from the output voltage UA (FIG. 2, 1st row), the integrator 7 integrates in the interval t1 down to the threshold US1. On reaching this threshold value the logic 9 switches over the switches 4,8 and 13. The light source 2 now lights up and the integrator 7 integrates in the interval t2 upwards to the threshold value US2, on reaching which the circuit is once again reset to the critical state (time interval t3) and the cycle begins again.

Thus, for both light sources with the light circuit the radiated light quantity is set at a particular value which, as shown in FIG. 2, row 1, can be different in the spectral areas. Thus, a standardization of the intensity irradiated by the light sources is carried out, i.e. the reference receiver 6 functions as quantum counter by summation (integration with respect to the received intensity and time). Thus the quantum quantity radiated from the light sources, the light-emitting diodes, is defined and forms the value $I_0$ of the absorption formula according to Lambert-Beer Law. Temperature fluctuations of the light sources are thus not disturbingly noticeable in the measuring result, and nor are other interference factors influencing the instantaneous value of the intensity.

The measuring circuit is periodically switched over synchronously with the light circuit. Via the changeover switch 13, a signal is thus alternatingly applied to the integrator 12, and is respectively proportional to the light influenced by the specimen in the two wavelength areas.

The voltage curve UE corresponding to the periodical switching on of the light sources at the output of the integrator 12 in the measuring circuit of FIG. 1 is illustrated in FIG. 2 in the 2nd row for different cases. In the intervals t1 to t4 the signal at the measuring receiver 5 is not influenced by the specimen. In the interval t5 the one light colour is attenuated and in the interval 7 the other light colour. In the intervals t10 and t11 an absorption occurs in both spectral areas.

In the example hemoglobin the absorption of the transmitted radiation with green light is large, whereas the absorption in the red area is comparatively small. By comparing the absorption rates at the different wavelengths the occurrence of hemoglobin can thus be determined.

The evaluation logic 16 determines in dependence on the exceeding or the non-attainment of the threshold value US3 and US4 the different absorption in the two spectral areas and emits a signal at the output 16a on presence of a typical combination, e.g. the information on hematocrit and hemolysis values when the arrangement is used for the detection of hemoglobin or red blood cells in plasma or in other fluids.

For the realization of the circuits a great variety of solution possibilities are known to the expert. Thus, for example, the changeover switch and the sign reversing member can respectively be incorporated into the integrator. Then a reversible indicator in the integration direction is obtained.

The component parts, including the light sources, are preferably modern electronic components i.e. the light sources are formed by light-emitting diodes.

Preferably a double light-emitting diode is used according to FIG. 3a. A light source 2 for green light and a light source 3 for red light are disposed in a transparent housing 18 with a diffusely scattering front part 17. The double light-emitting diode sends light through the specimen 1 to the measuring receiver 5. A part of the light is scattered to the reference receiver 6 in the diffusely scattering front part 17. A schematic representation of this arrangement according to FIG. 3a is illustrated in part b of the Figure. FIG. 3c shows a further possible arrangement of the measuring apparatus which manages without the diffusion disk 17 and which corresponds to the arrangement according to FIG. 2.

The measuring apparatus is preferably connected in such a manner that the light sources and the light receivers, including the specimen, are housed in a compact measuring cell. To the first approximation it can thus be assumed that all components are exposed to the same alterations as regards temperature, contamination or condensation, ageing etc., which advantageously affects the measuring accuracy.

Should phototransistors be used as photoelectric receivers, then expediently one of the contact-break distances of the changeover switch lies in the collector circuit and the other in the emitter circuit. The contact-break distances are alternately connected with either a pole of the supply voltage or with the input of the integrator.

The evaluation logic 16 comprises advantageously limit switches which produce a signal on extreme ratios of the output voltage to the threshold values, e.g. with strong pacifying with which an alarm can be produced or the arrangement switched off.

The switchover frequency is preferably at 4 Hz; it can however also be chosen higher or lower.

We claim:

1. An apparatus for photometrically investigating substances according to a two wavelength-method, in particular, for determining hemoglobin and other colored substance content in a substance specimen of blood plasma and blood serum, the apparatus comprising:
    a first light source having a first wavelength of emission within a first range of absorption levels of the substance specimen;
    a second light source having a second wavelength of emission within a second range of absorption levels of the substance specimen;
    means for alternatingly activating said first and second light sources, said activating means including a first switch-over device and a second switch-over device;
    a measuring photodetector means and a reference detector means, said measuring photodetector means and said reference photodetector means each for detecting emissions from both said first light source and said second light source, said measuring detector means for detecting light transmitted through the substance specimen and said reference photodetector means for detecting light directly from said first light source and said second light source; and
    evaluation means coupled to said measuring and said reference photodetector means for determining the different absorption typical for the substance specimen, in both the first light wavelength and the second light wavelength, including means for determining exposure of light respectively transmitted by the first and second light sources to establish a first switch-over point in time for said first switch-over device for controlling said first light source upon attainment of a first predetermined exposure of light and to establish a second switch-over point in time for said second switch-over device for controlling said second light source upon attainment of a second predetermined exposure of light.

2. The apparatus according to claim 1 including light-emitting diodes as said light sources with a transparent housing (18) and a diffusely dispersing front part (17).

3. The apparatus according to claim 2 wherein said first light source and said second light source comprise a double light-emitting diode.

4. The apparatus according to claim 1, wherein the light sources, the photodetector means and the specimen sample are disposed in a compact measuring cell.

5. The apparatus according to claim 1, wherein the predetermined light exposure are different in the two spectral regions.

6. The apparatus according to claim 1, wherein the light source changeover frequency lies at 4 Hz.

7. The apparatus according to claim 1 wherein said evaluation means further comprises:
    first means, including a first logic means, coupled to said reference detector means for selectively inverting polarity of electrical signals received through said reference detector means under control of said first logic means and coupled to said measuring detector means for selectively inverting polarity of electrical signals received through said measuring detector means under control of said first logic means;
    first integrator means coupled alternately to said first inverting means and to said reference detector means by means of said first switch-over device for integrating signals received from said reference detector means both directly and through said first inverting means;
    first comparator means coupled to said first integrator means, said first comparator means including means for establishing a first threshold value and a second threshold value which predefine light limits that, when exceeded, provide a logic signal to said first logic means;
    first integrator means coupled alternately to said second inverting means and to said measuring detector means by means of said second switch-over device for integrating signals received from said measuring detector means both directly and through said second inverting means;
    second comparator means coupled to said second integrator means, said second comparator means including means for establishing a third threshold value and a fourth threshold value which predefine light limits that, when exceeded, provide a logic signal to said first logic means; and
    a second logic means coupled to said first comparator means and to said second comparator means for evaluating the output signal magnitudes of the first and second integrators to determine the different absorption in first and second spectral regions.

8. The apparatus according to claim 7, wherein the second logic means (16) comprises limit value switches which generate an alarm and/or switch-off signal at extreme ratios of the output signals to the threshold values.

9. The apparatus according to claim 7, wherein the first switch-over device is coupled to the input of the first integrator means and the second switch-over device is coupled to the input of the second integrator means, and wherein each inverting means comprises a sign reversing circuit so that said first and second switch-over device is alternately coupled to the output of one photo detector and the output of one reversing circuit.

10. The apparatus according to claim 9, comprising phototransistors as photoelectric receivers, wherein in each case in the collector and emitter circuit a contact-break distance of the change-over switch lies between the poles of a supply voltage and an associated electrode in such a manner that respectively, switchable between the poles, one contact-break distance is connectable to the supply voltage and the other contact-breaking distance to the input of the integrator.

* * * * *